(12) United States Patent
Gorsuch et al.

(10) Patent No.: US 7,481,936 B2
(45) Date of Patent: *Jan. 27, 2009

(54) METHOD AND APPARATUS FOR PATIENT FLUID MANAGEMENT

(75) Inventors: Reynolds G. Gorsuch, Yountville, CA (US); Harold H. Handley, Encinitas, CA (US); Harold W. Peters, Martinez, CA (US)

(73) Assignee: Transvivo Inc., Yountville, CA (US)

( * ) Notice: Subject to any disclaimer, the term of this patent is extended or adjusted under 35 U.S.C. 154(b) by 297 days.

This patent is subject to a terminal disclaimer.

(21) Appl. No.: 11/078,016

(22) Filed: Mar. 11, 2005

(65) Prior Publication Data

US 2005/0215936 A1 Sep. 29, 2005

Related U.S. Application Data

(63) Continuation-in-part of application No. 09/981,783, filed on Oct. 17, 2001, now Pat. No. 6,899,692.

(51) Int. Cl.
*B01D 61/14* (2006.01)
*B01D 61/18* (2006.01)
*B01D 63/02* (2006.01)
*B01D 63/04* (2006.01)
B01D 61/00 (2006.01)
B01D 63/00 (2006.01)

(52) U.S. Cl. .................. 210/645; 210/646; 210/650; 210/651; 210/321.69; 210/321.71; 210/321.88; 210/321.79; 210/500.23; 604/5.01; 604/6.01; 604/6.09

(58) Field of Classification Search .................. None
See application file for complete search history.

(56) References Cited

U.S. PATENT DOCUMENTS 4,235,231 A 11/1980 Schindler et al.

(Continued)

FOREIGN PATENT DOCUMENTS

EP 0 321 448 A2 6/1989

(Continued)

OTHER PUBLICATIONS

A. Sueoka, Present Status of Apheresis Technologies: Part 2. Membrane Plasma Fractionator, *Therapeutic Apheresis*, vol. 1, No. 2, pp. 135-146, May 1997.

(Continued)

*Primary Examiner*—Krishnan S Menon
(74) *Attorney, Agent, or Firm*—Knobbe Martens Olson & Bear LLP (57) ABSTRACT

Patient fluid management is carried out by separating plasma from whole blood in vivo via an implantable filter device comprising one or more elongated hollow tubes and a plurality of elongated microporous fibers having an interior lumen extending along the length thereof, each fiber having a first and second end secured to the one or more elongated hollow tubes by passing plasma through the fiber wall from the outer wall surface to the inner wall surface and to the interior fiber lumen, directing the separated plasma to an ultrafiltration apparatus having a sieving coefficient cutoff between about $1 \times 10^4$ and about $6 \times 10^4$ daltons, separating plasma water and selected plasma components, from the separated plasma, and directing the treated plasma to the patient.

44 Claims, 3 Drawing Sheets

U.S. PATENT DOCUMENTS

| | | |
|---|---|---|
| 4,440,641 A | 4/1984 | Ostertag |
| 4,769,146 A | 9/1988 | Schmidt |
| 4,832,034 A | 5/1989 | Pizziconi et al. |
| 4,950,224 A | 8/1990 | Gorsuch et al. |
| 5,145,583 A | 9/1992 | Angleraud et al. |
| 5,151,082 A | 9/1992 | Gorsuch et al. |
| 5,152,743 A | 10/1992 | Gorsuch et al. |
| 5,224,926 A | 7/1993 | Gorsuch et al. |
| 5,284,583 A | 2/1994 | Rogut |
| 5,605,627 A | 2/1997 | Carlsen et al. |
| 5,716,689 A | 2/1998 | Rogut |
| 5,735,809 A | 4/1998 | Gorsuch |
| 5,968,004 A | 10/1999 | Gorsuch |
| 5,980,478 A | 11/1999 | Gorsuch et al. |
| 5,980,481 A | 11/1999 | Gorsuch |
| 6,013,182 A | 1/2000 | Emi et al. |
| 6,102,884 A | 8/2000 | Squitieri |
| 6,224,765 B1 | 5/2001 | Watanabe et al. |
| 6,607,501 B2 * | 8/2003 | Gorsuch .................... 604/5.01 |
| 6,659,973 B2 * | 12/2003 | Gorsuch et al. ............ 604/6.04 |
| 6,899,692 B2 * | 5/2005 | Gorsuch et al. ............ 604/6.09 |
| 2002/0087109 A1 * | 7/2002 | Gorsuch et al. ............ 604/6.04 |

FOREIGN PATENT DOCUMENTS

EP     0 341 979 A2     11/1989

OTHER PUBLICATIONS

Ronco, et al., A Novel Approach to the Treatment of Chronic Fluid Overload with a New Plasma Separation Device, *Cardiology 2001*; 96:135-146, Jan. 2002.

Handley, et al., Intravenous Catheter for Intracorporeal Plasma Filtration, *Blood Purification 200*, 20:61-69, Jan. 24, 2002.

* cited by examiner

METHOD AND APPARATUS FOR PATIENT FLUID MANAGEMENT

RELATED APPLICATIONS

This application is a continuation-in-part of U.S. patent application Ser. No. 09/981,783, filed Oct. 17, 2001, now U.S. Pat. No. 6,899,692, incorporated by reference herein in its entirety.

BACKGROUND OF THE INVENTION

Apparatus and methods currently used for carrying out patient fluid management require whole blood to be removed from the patient and processed in two ex-vivo stages. In a first stage the blood is processed to separate plasma, and in a second stage the plasma is processed in an ultrafiltration apparatus to remove plasma water and toxins. Although such procedure reduces the blood volume to normality, thereby treating fluid overload, the procedure causes massive change in blood hemodynamics in a short period of time including producing heavy stress on the human system with severe fluctuations and blood pressure and trauma to other body organs. Moreover, whole blood removal results in the necessity to heparinize or anticoagulate the patient to minimize clotting in the ex-vivo circuit and apparatus. Such treatment is counter-indicated in most surgical patients and deleterious to others due to consequential damage to blood components and the removal of vital blood components unrelated to the therapy. Removing and treating whole blood ex-vivo dictates that the procedure be a "batch" or intermittent process with attendant loss of efficiency and confinement of the patient to a clinical setting where support systems and machinery are available. Removal of whole blood also exposes the patient to contamination by viral and/or bacterial infection from nosocomial sources, and removal of erythrocytes, platelets and other large cellular blood components exposes them to risk of damage due to mechanical and chemical exposure to non-biocompatible surfaces of ex-vivo apparatus.

SUMMARY OF THE INVENTION

The present invention relates to a method and apparatus for carrying out patient fluid management including acute and chronic fluid overload without removing whole blood from the patient. The apparatus includes a filter device for being implanted in a blood vessel for carrying out in-vivo plasma separation using a plurality of elongated hollow fibers having an asymmetrical fiber wall morphology in which the inner wall surface along the interior fiber lumen has a lower mass density and the fiber wall adjacent to the outer wall surface has a higher mass density. Plasma is separated from whole blood in-vivo by passing through the fiber wall from the outer wall surface to the interior fiber lumen. The filter device comprises one or more elongated hollow conduits or tubes to which opposite ends of each of the fibers are secured so that the interior of the one or more hollow tubes communicates with the interior lumen of each of the elongated hollow fibers. The fluid management apparatus includes a multiple lumen catheter, secured to the proximal end of the one or more hollow tubes, for directing the in-vivo separated blood plasma from the filter device to an ultrafiltration apparatus in which plasma water and selected plasma components are separated and removed from the plasma. The treated plasma is returned to the patient. A preferred ultrafiltration apparatus has a sieving coefficient cutoff below about $6 \times 10^4$ daltons. The apparatus also includes piping and cooperating pumps for directing plasma between system components as well as backflush components comprising piping, backflush pump and source of backflush fluid selectively directed to the filter device for a duration and flow rate sufficient to substantially cleanse filter pores. In a preferred embodiment, operation of the apparatus is controlled by a microprocessor/controller.

DETAILED DESCRIPTION OF THE PREFERRED EMBODIMENTS

Figure 1:
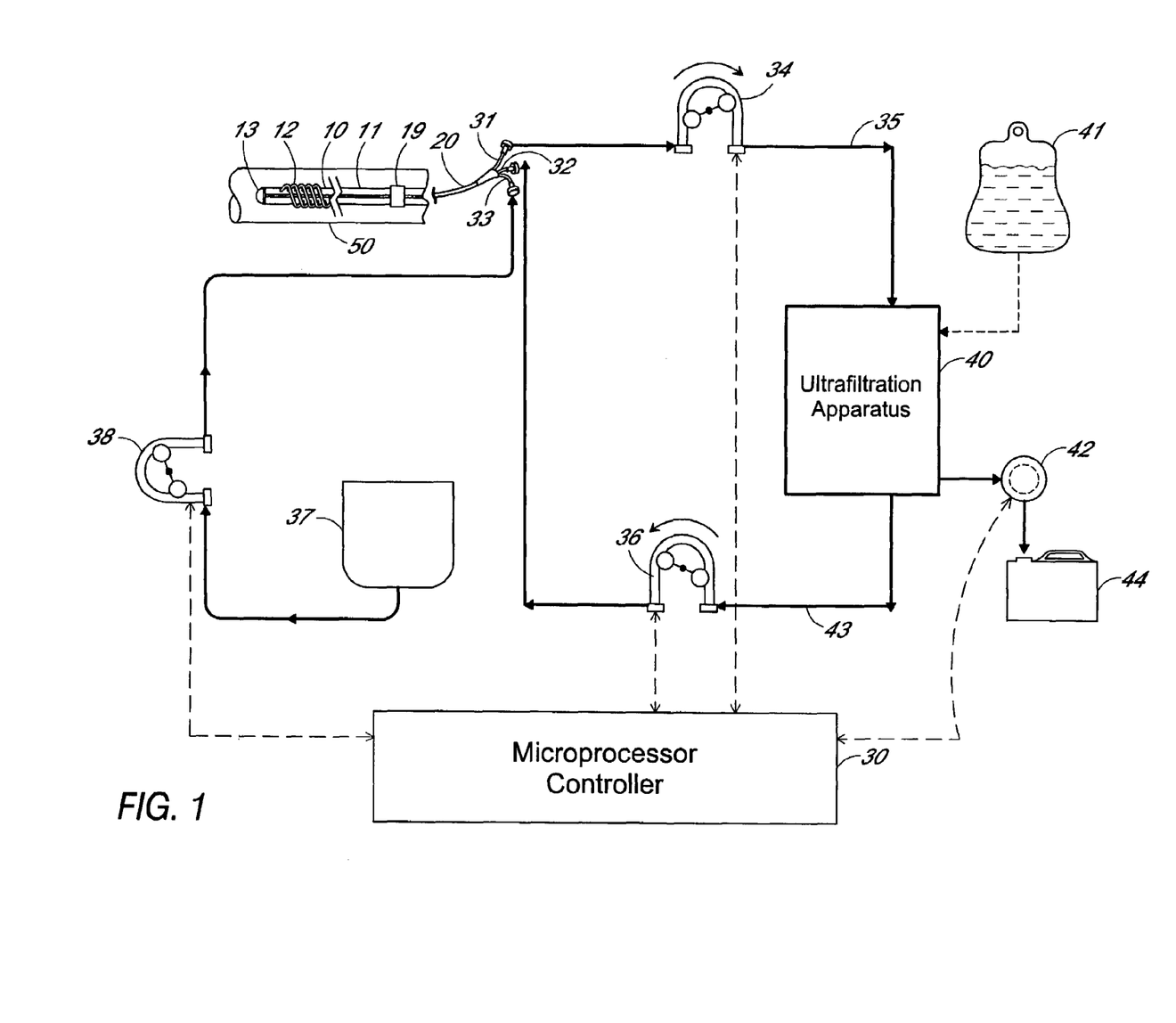
FIG. 1 is a schematic illustration of a preferred embodiment of an apparatus for carrying out patient fluid management.

The preferred embodiment of an apparatus for carrying out patient fluid management according to the invention schematically illustrated in FIG. 1 includes a filter device 10, a multiple lumen catheter 20, an ultrafiltration apparatus 40, a fluid control assembly including tubing and pumps, and a microprocessor/controller 30. The filter device 10, which will be described in more detail hereinafter, is implantable in the vasculature of a patient or animal in which in-vivo plasma separation is to be carried out. Examples of veins suitable for implanting the filter include the superior or inferior vena cava or the subclavian vein. In the drawing, the filter device 10 is shown implanted in a blood vessel 50.

Figures 7, 8:
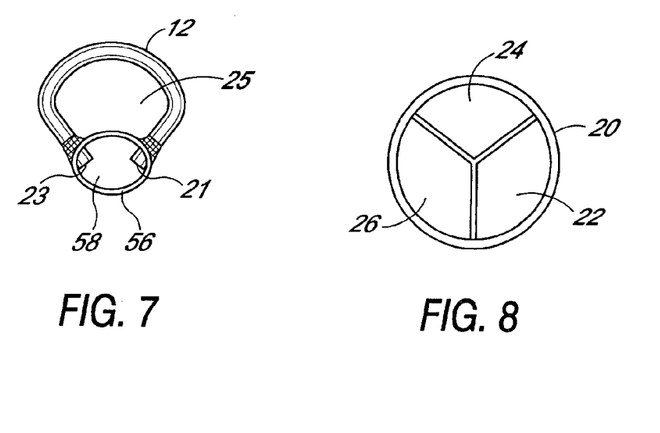
FIG. 8 is a sectional view of a triple lumen catheter of the apparatus shown in FIG. 1 illustrating the catheter interior.

The filter device 10 is used in combination with a multiple lumen catheter, preferably a triple lumen catheter 20 as illustrated in FIG. 8. The catheter is of a suitable length to provide for implanting or installing the filter device into the appropriate vessel of the patient, e.g., the inferior vena cava, between the diaphragm and the iliac junction via the femoral vein, jugular vein or subclavian vein. The catheter 20 may be secured to the proximal end 17 of the filter device 10 by a suitable method, e.g., using a suitable adhesive and an injection-molded connector 19. The catheter 20 has an access lumen 26 which is in open fluid communication with the interior of elongated hollow tubes 14 and 16 of the filter device. Return lumen 22 is occluded or blocked off at the distal end of the catheter 20, and is provided with one or more ports through the catheter wall near the distal end of the catheter whereby treated plasma may be returned to the patient. Backflush lumen 24 is also in open fluid communication with the interior of the hollow tubes 14 and 16 through which periodic backflush fluid is directed for preventing occlusion of the hollow fiber membrane caused by blood components. Plasma is separated from whole blood within the blood vessel in which the filter device is inserted using trans-membrane pressure (TMP) supplied by access pump or first pump 34, a positive displacement volumetric pump that operates to regulate pressure and control trans-membrane pressure and plasma volume removal rate.

Figures 2, 3, 4:
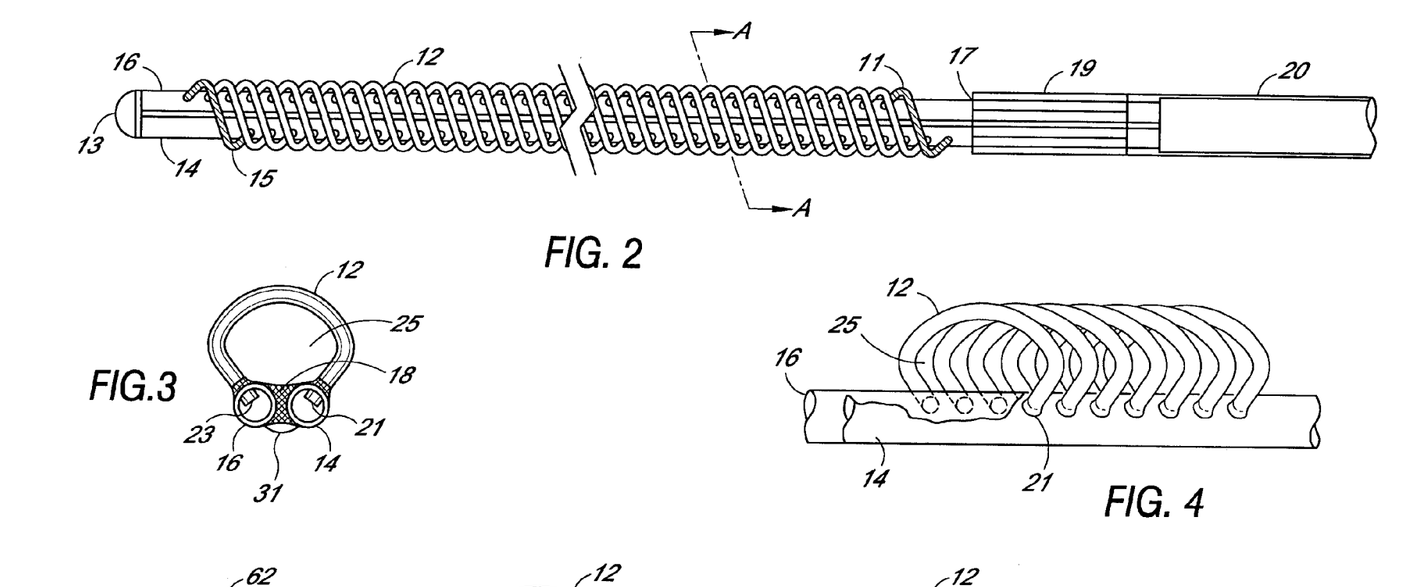
FIG. 2 is a top view of a preferred embodiment of a filter device shown in FIG. 1 for separating plasma from blood in-vivo having a pair of elongated hollow tubes joined together along their length, showing distal and proximal end segments.
FIG. 3 is an enlarged sectional view of the filter device of FIG. 2 along the lines A-A showing a single elongated hollow fiber secured to the hollow tubes.
FIG. 4 is an enlarged view of a portion of the filter device shown in FIG. 2.

Plasma separated from whole blood through the microporous fibers 12 of the filter device is directed through access lumen 26 and first tubing 31 to ultrafiltration apparatus 40 for separating and removing plasma water and selected plasma components from the plasma. Plasma water and plasma components removed from the treated plasma may be directed to a container 44. An effluent pump 42 is optional and may be advantageously used for assisting in controlling the rate of plasma water removed by providing controlled trans-membrane pressure across filter membranes of the ultrafiltration apparatus. Plasma is returned to the patient via tubing 43 at a rate controlled by pump 36. The tubing 43 is in fluid communication with plasma return tube 32 which is connected to plasma return lumen 22 of triple lumen catheter 20 (FIG. 4).

The ultrafiltration apparatus 40 for treating the plasma removed in vivo by the previously described filter apparatus and filter device may be a conventional ultrafiltration apparatus used for separating plasma water from blood utilizing conventional hemodialysis apparatus and procedures. Such apparatus is known to those skilled in the art and is described, for example, in U.S. Pat. No. 5,605,627, the description of which is incorporated herein by reference. A commercial example of such ultrafiltration apparatus is MINNTECH HEMOCOR HPH 400TS®. The ultrafiltration apparatus is capable of and configured for removal of metabolic toxic waste including plasma water to carry out the desired patient fluid management. The make-up of blood and plasma components by molecular weight in daltons is shown in Table 1. A preferred ultrafiltration apparatus is configured to remove and separate plasma components having a molecular weight below the molecular weight of albumin ($6.9 \times 10^4$). Removal of substantial or excessive amounts of albumin is to be avoided to prevent hypoalbuminemia. Albumin replacement is expensive as is removal of other important immune system proteins, as will be understood by those skilled in the art. Thus, although an ultrafiltration sieving coefficient cutoff between about $1 \times 10^4$ and about $1 \times 10^5$ daltons could be used, it is preferred that the ultrafiltration sieving coefficient cutoff is less than about $6.9 \times 10^4$, and more preferably less than about $6 \times 10^4$ daltons. Any ultrafiltration apparatus capable of separating and removing plasma water and components within the aforesaid ranges may be used. Preferred plasma separation filter cutoff (sieving coefficient cutoff) is above ultrafiltration cutoff and below about $5 \times 10^6$ daltons, and preferably between about $6 \times 10^4$ and about $2 \times 10^5$ daltons.

The preferred apparatus shown in FIG. 1 includes backflush fluid reservoir 37, backflush pump 38 and backflush tube 33 communicating with a backflush lumen of the multiple lumen catheter. Such backflush components and method are disclosed in U.S. Pat. No. 6,659,973, the description of which is incorporated herein by reference in its entirety. Backflush pump 38 is selectively and periodically operated to provide backflush fluid flow for substantially cleansing the pores of the fiber membrane of the filter device. Such a backflush cycle is preferably operated at high trans-membrane pressure and low volume and at relatively short injection times for backflushing whereby the membrane pores of the filter device are temporarily expanded and flushed to dislodge adhered proteins, thereby restoring pore integrity and density of the virtual filter area for improved plasma separation performance after each backflush cycle.

Fluid control of plasma within the apparatus may be controlled using a microprocessor/controller operatively communicating with the positive displacement volumetric pumps for controlling trans-membrane pressure in the filter device, plasma removal rate, plasma return rate and backflush pressure and rate. Such fluid control and management may be selected, tailored or designed for slow, continuous acute fluid removal. For example, operation of the system may be used for controlling plasma extraction rate from blood to achieve removal of 1-2 L, or more, of plasma water over a 24-hour period. The fluid control assembly may also include volume sensors, pressure sensors, blood leak detectors and air detectors connected to the piping and reservoirs as desired. As illustrated in FIG. 1, the microprocessor/controller 30 is operatively connected to the pumps. Similarly, the microprocessor/controller operates for controlling backflush pump 38 and plasma is returned at a selected rate by controlling pump 36. The microprocessor/controller may be programmed for flow rates designed to a the prescribed patient therapy. Plasma fluid control may also require the infusion or addition of fresh plasma fluid to compensate for excess plasma water loss. In the embodiment shown in FIG. 1, a source of fresh plasma fluid 41 provides such fluid which may be introduced via the ultrafiltration apparatus or the plasma return line.

In a preferred embodiment illustrated in FIGS. 2 and 3, a pair of elongated hollow tubes are joined side-by-side lengthwise to form the core of the filter device. The two elongated hollow core tubes 14 and 16 terminate at a distal end with a distal end plug or cap 13 formed of a material that seals the open tube ends. The tubes and end cap may be made of any suitable biocompatible material, for example, medical grade extruded urethane tubes. Other biocompatible materials include synthetic rubbers, polycarbonate, polyethylene, polypropylene, nylon, etc. The elongated hollow tubes may be secured together using suitable bonding material 18, adhesive compositions, etc., for example, a UV curable adhesive applied along the length between the two tubes. The length and diameter of the filter device may be selected to accommodate the vessel or vein in which it is to be implanted. Accordingly, the diameter and length of the one or more elongated hollow tubes forming the central core of the filter device are selected. A suitable tube length is between about 15 cm and about 25 cm, and preferably between about 18 cm and about 22 cm. Where a pair of core tubes is used as shown in the preferred embodiment, an outer diameter of each tube of between about 1 mm and about 3 mm is suitable. A detectable marker component 31, e.g., a radio opaque material may also be bonded to the device, for example, in bonding material 18 extending along the length of the tubes to assist in implanting and/or monitoring the device especially during insertion and removal.

The elongated hollow microporous fibers used in the filter device are the asymmetrical wall fibers disclosed in U.S. Pat. No. 6,802,971, the description of which is incorporated herein by reference in its entirety. The morphology of the fiber walls is asymmetrical between the inner fiber lumen and the outer fiber wall which is in direct contact with the blood flowing in the vasculature in which the device is implanted. The filtration performance of such a device is a function of the filter surface of the exposed fibers whereby consideration is given to use larger diameter fibers and to maximize the number of fibers. Thus, it may be desirable to use as many individual fibers along the hollow core tubes of the filter device as is practical while maintaining separation of the individual fibers to provide for fluid flow therebetween, and to maximize the amount of outer fiber surface exposed to blood flowing along the length of the filter device. Moreover, the fibers are secured along the length of the hollow tubes in such a manner as to form a fluid flow space between the fibers and the tubes. Again, however, the length of the filter device as well as the overall cross-sectional dimension are tailored or dictated by the blood vessel in which the device is to be used so as to avoid substantial interference with blood flow through the vessel while at the same time be efficient to achieve the intended flow rate of separated plasma.

In a preferred embodiment, the ends of each of the fibers are offset longitudinally relative to one another as illustrated in FIGS. 2 and 3. As shown, elongated hollow fiber 12 has a first end 21 secured in first elongated hollow tube 14 and second end 23 secured in second hollow tube 16. In the specific device illustrated, the longitudinal spacing between the first and second ends of each fiber is a three-hole or three-fiber offset, e.g., about 0.5 cm. However, with intervals between the adjacent fiber ends of between about 0.1 cm and about 1.0 cm, offsets between first and second fiber ends may be between about 0.3 cm and about 3.0 cm, by way of example. With such offsets between first and second fiber ends, a straight line extending between the ends of a fiber forms an acute angle with an elongated axis of either or both of the elongated hollow tubes, and whereby the fibers also extend lengthwise between their ends along an angle other than 90° relative to the axes of the elongated hollow tubes. The acute angle preferably is between about 45° and about 85°. However, other fiber angles including 90° are not precluded and may be used where desired. In another preferred embodiment shown in FIG. 2, the proximal and distal fibers 11 and 15 located at each end of the filter device are filled with polyurethane or other biocompatible synthetic resin composition. These solid fibers at the ends of the row of fibers protect the adjacent hollow fibers from potential damage caused by mechanical stress during catheter insertion and removal.

In an example of assembly of a filter device, the elongated hollow core tubes 14 and 16 are joined as previously described and holes are drilled at the desired spacing along each of the two tubes. The holes may be drilled along opposite sides of the two tubes, and preferably are spaced at regular intervals of between about 0.1 cm and about 1.0 cm, and more preferably between 0.1 cm and about 0.3 cm. In a device as illustrated in FIGS. 1-3, 6 fibers/cm are used and the interval or spacing between fiber ends along each of the tubes is approximately 1.66 mm. However, other practicable fiber spacing may be used, for example, between about 4 and about 8 fibers/cm and preferably between 5 and 7 fibers/cm of the length of the hollow tubes. The fibers may be secured in the spaced holes by any suitable method. For example, a first fiber end is inserted in a first hole in one of the tubes, the tubes are rotated 180°, and a second end of the fiber inserted in a first hole in the other tube. The procedure is repeated until all fiber ends are inserted in the holes along the two joined tubes. A wire or other elongated member may be inserted along the interior of each of the core tubes during assembly to provide a uniform limit or stop for the fiber ends along the respective hollow tube interior passageways. The fibers are bonded to the tubes and the joints between the fibers and the tubes sealed using a suitable adhesive or potting compound and the wires are removed. In the specific example of a filter device shown in FIG. 1, 118 active hollow fibers and 2 filled end fibers are spaced at 6 fibers/cm along 20.4 cm of the tubes. Each fiber is about 1.5 mm long.

Figure 5:
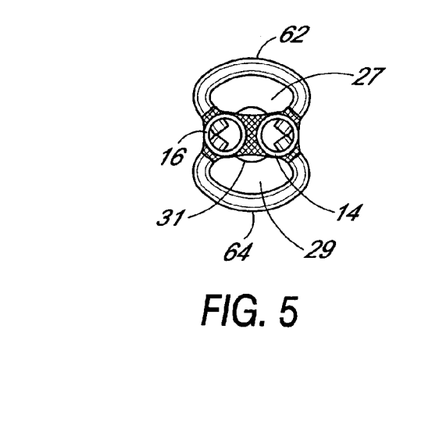
FIGS. 5-7 are sectional views of other filter device embodiments.

FIG. 5 illustrates an alternative embodiment in which fibers are positioned on two sides of the filter device. Fibers 62 and 64 extend at opposite sides of the device whereby first and second ends of each of the fibers are secured along two rows along each of the tubes. As shown in FIGS. 3-5, the fibers are arched to form a space between the fibers and the elongated tubes. In FIGS. 3 and 4, a space 25 is formed by the arched fibers, and in FIG. 5, two spaces 27 and 29 are formed by the arched fibers on both sides of the filter device. The length of the fibers may be selected to accommodate the desired filter surface, as well as the desired cross-sectional dimension of the filter device as previously discussed. Suitable fiber lengths are between about 1 mm and about 4 mm to provide sufficient space between the arched fibers and the hollow tubes without distorting the fibers which could cause undesirable strains along the fiber walls or otherwise compromise fiber performance.

Figure 6:
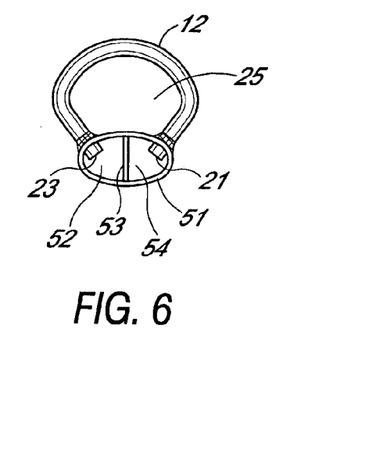

FIGS. 6 and 7 illustrate alternative filter device design embodiments. In FIG. 6, a single tube 51 having a divider wall or septum 53 extending the length of the tube separates two elongated chambers 52 and 54. Another plasma separation filter design is illustrated in FIG. 7 utilizing a single tube 36 having one elongated hollow passageway 58 extending along the tube. Such alternative filter devices are produced, assembled and function substantially as previously described for the two-tube embodiment.

Figure 9:
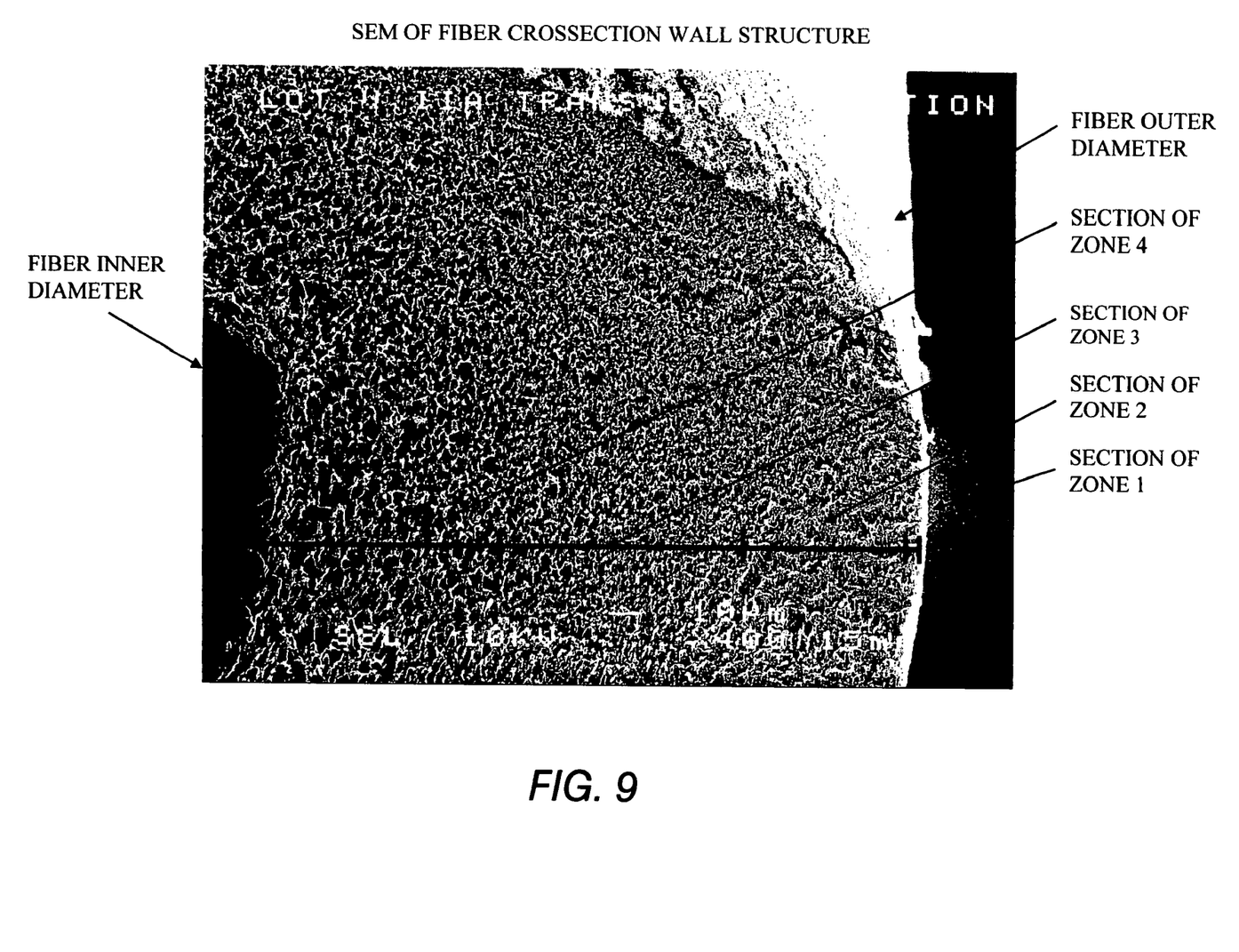
FIG. 9 is a scanning electron microscopy (SEM) image of a cross-section of a preferred elongated hollow fiber wall used in a filter device shown in FIG. 2 at 400× magnification.

As previously stated, the plasma separation filter device utilizes elongated microporous fibers having asymmetrical fiber wall structure between the inner wall surface extending along the interior fiber lumen and the outer fiber wall surface exposed to blood in the vessel in which the filter device is implanted. The fiber wall at or adjacent to the outer wall surface has a higher mass density than the mass density adjacent to or at the inner wall surface. The mass density is a function of the average nominal pore size. Such asymmetric fiber wall morphology is illustrated in FIG. 9 showing a scanning electron microscopy (SEM) image of a cross-section of the fiber at 400× magnification. It will be observed That the structure of the fiber from the outer surface to the lumen is a continuous change in mass density whereby the pore size gradually changes between these fiber wall surfaces. The fiber walls are also characterized by a substantially uniform wall thickness between the inner and outer wall surfaces and comprises a continuum of voids bounded by solid frames and substantially without macrovoids other than the pores, as shown. It may be convenient to describe the continuum of different mass density as sections or zones of the wall area having an average nominal pore size or average pore diameter, each zone having a different average nominal pore size. Thus, the walls may be characterized by two or more zones, for example 2, 3, or 4 or more mass density zones. In the fibers, the outer surface of the membrane, zone 1, has the highest mass density characterized by smaller average pore diameters. The outer zone forms the fiber interface with the permeate blood flow by determining filtration characteristics including the composition and components of separated plasma and controlling fiber membrane performance. Thus, zone 1 is the principle filtration portion of the fiber wall for controlling the trans-membrane flux (TMF) for excluding even the smallest cells in the blood, the platelets, having a diameter of about 1 µm. Nominal average pore diameters in zone 1 are between about 0.3 µm and about 1 µm. and preferably range from about 0.4 µm to about 0.8 µm. A preferred filtration sizing has a cutoff of about 0.6 µm to about 0.8 µm. Zones 2 and 3 are designed to decrease the flow path tortuosity and maintain the structural integrity required of the fiber exposed to physical conditions within the body. Pore size distribution in these zones ranges gradually from about 0.8 µm to about 1.2 µm and from about 1.2 µm to about 2.0 µm. Zone 2, having some flux-controlling pores, is principally to provide structural strength to the fiber as well as acting as a conduit for exudate flow to zone 3, also providing structure and enlarged pores for reducing the hydraulic resistance and providing a fluid conduit to the fiber lumen. The interior zones have little filtration function. Zone 4, representing the largest area having relatively large voids and pore diameters with little solid structure, has the primary function of a major reduction of hydraulic resistance through the membrane and defines the fiber inner lumen surface. Nominal average pore diameters in this lowest mass density zone are between about 1 μm and about 60 μm, and preferably between about 2 μm and about 6 μm. A typical fiber as shown has an CD of about 650 μm, an ID of about 250 μm and a wall thickness of about 250 μm. However, such dimensions are by way of example only. Again, such fibers are more filly described in U.S. Pat. No. 6,802,971.

The elongated microporous fibers used in the filter device may be produced using biocompatible polymers including those produced from polyurethane, polypropylene, polysulfone (polyethersulfone), polycarbonate, nylon, polyimide, as well as other synthetic resins known to those skilled in the art. A preferred polymer is polysulfone, and more preferably a polyethersulfone/polvethylene oxide copolymer with a polyethylene glycol solvent or a polysulfone modified with polyethylene oxide-polyethylene glycol copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. Specific methods for producing the aforesaid polymers and fibers are known to those skilled in the art and disclosed, for example, in PCT Publication WO 90/04609.

The advantages of using the methods and apparatus described above for patient fluid management over conventional procedures include elimination of the disadvantages of the removal of whole blood from the body and subsequent ex-vivo plasma separation and ultrafiltration. The in-vivo plasma extraction technique permits a new approach to extracorporeal therapies especially useful and beneficial for the treatment of chronic fluid overload as well as for acute conditions such as patients having congestive heart failure. The in-vivo separation of plasma may reduce blood damage and loss, simplify the extracorporeal circuit and permit operation with lower pressures and less heparinization in the extracorporeal circuit. The absence of red cells in the extracorporeal circuit will eliminate thrombosis and may result in a better and longer utilization of the external filter and potential reduction in cost. In-vivo plasma separation permits continuous real time therapy in most applications with resultant improvement in effectiveness, and in many applications would result in the ability to perform the therapy in a home setting or ambulatory mode which could be a major improvement in patient lifestyle as well as economy for the medical care system. Moreover, the use of the methods and apparatus described herein would increase the capacity of most caregiver organizations which are now limited by patient load capacity including the number of centrifuge machines available in the facility.

TABLE 1

BLOOD AND PLASMA COMPONENTS
SIZE BY MOLECULAR WEIGHT (DALTONS)

| COMPONENT | $\leq 10^3$ DAL. | $\leq 10^4$ DAL. | $\leq 10^5$ DAL. | $\leq 10^6$ DAL. | $\geq 10^6$ DAL. |
|---|---|---|---|---|---|
| ELECTROLYTES | | | | | |
| H$_2$O | 18 | | | | |
| Sodium | 22.89 | | | | |
| Magnesium | 24.3 | | | | |
| Chloride | 35.4 | | | | |
| Potassium | 39.1 | | | | |
| Calcium | 40.0 | | | | |
| NaCl | 58.5 | | | | |
| Urea | 60.0 | | | | |
| Glysine (smallest amino acid) | 75.0 | | | | |
| Creatinine | 113.1 | | | | |
| Uric Acid | 168.1 | | | | |
| Glucose | 180 | | | | |
| Dextrose | 180.1 | | | | |
| Triptophane (largest amino acid) | 204.2 | | | | |
| Sucrose | 342 | | | | |
| Billirubin | 584.6 | | | | |
| Haptens | <1 × 10$^3$ | | | | |
| PROTEINS (74 g/L mean-adults) Low flux Dialyzer cut-off | | | | | |
| Inulin | | 5 × 10$^3$ | | | |
| Amyloid A protein | | 8 × 10$^3$ | | | |
| β$_2$-Microglobulin | | | 1.18 × 10$^4$ | | |
| Lisophospholipase | | | 1.3 × 10$^4$ | | |
| IL-2 Interleukin | | | 1.55 × 10$^4$ | | |
| CD 3 (T3ξ) membrane complex | | | 1.6 × 10$^4$ | | |
| Myoglobin | | | 1.76 × 10$^3$ | | |
| J-chain | | | 1.76 × 10$^4$ | | |
| IL-5 Interleukin | | | 1.8 × 10$^4$ | | |
| M-CSF | | | 1.8 × 10$^4$ | | |
| Serum amyloid A component | | | 2.0 × 10$^4$ | | |

TABLE 1-continued

BLOOD AND PLASMA COMPONENTS
SIZE BY MOLECULAR WEIGHT (DALTONS)

| COMPONENT | $\leq 10^3$ DAL. | $\leq 10^4$ DAL. | $\leq 10^5$ DAL. | $\leq 10^6$ DAL. | $\geq 10^6$ DAL. |
|---|---|---|---|---|---|
| IL-4 Interleukin | | | $2.0 \times 10^4$ | | |
| CD3 (T3δ, ε) membrane complex | | | $2.0 \times 10^4$ | | |
| IL-6 Interleukin | | | $2.1 \times 10^4$ | | |
| Retinol binding protein | | | $2.12 \times 10^4$ | | |
| $C_8 \gamma$ complement protein | | | $2.2 \times 10^4$ | | |
| IL-3 Interleukin-3 | | | $2.2 \times 10^4$ | | |
| Factor D | | | $2.4 \times 10^4$ | | |
| Flagellin | | | $2.5\text{-}6 \times 10^4$ | | |
| CD3 (Tγ) membrane complex | | | $2.5 \times 10^4$ | | |
| $\alpha_1$-Microglobulin | | | $2.5\text{-}3.3 \times 10^4$ | | |
| C1s Complement protein | | | $2.7 \times 10^4$ | | |
| Class II histocompatibility molecules | | | $2.7\text{-}3.4 \times 10^4$ | | |
| CD3 (T3 ω) membrane complex | | | $2.8 \times 10^4$ | | |
| G-CFS | | | $3.0 \times 10^4$ | | |
| 9.5 S-α Glycoprotein | | | $3.08 \times 10^4$ | | |
| Li Invariant chain | | | $3.1 \times 10^4$ | | |
| IL-1 Interleukin-a | | | $3.1 \times 10^4$ | | |
| Urokinase Low H form | | | $3.3 \times 10^4$ | | |
| Thrombin | | | $3.3 \times 10^4$ | | |
| $C_{3d}$ complement protein | | | $3.3 \times 10^4$ | | |
| Apolipoprotein E | | | $3.3 \times 10^4$ | | |
| Erythropoietin | | | $3.4 \times 10^4$ | | |
| $\beta_2$-Glycoprotein III | | | $3.5 \times 10^4$ | | |
| Transcobalamin II | | | $3.8 \times 10^4$ | | |
| Factor I β | | | $3.8 \times 10^4$ | | |
| Interferon γ | | | $4.0 \times 10^4$ | | |
| $Z_n.\alpha_2$-Glycoprotein | | | $4.1 \times 10^4$ | | |
| Actin filaments | | | $4.2 \times 10^4$ | | |
| Protein A | | | $4.2 \times 10^4$ | | |
| Class 1 histocompatibility moleule | | | $4.4 \times 10^4$ | | |
| $\alpha_1$-Acid glyoprotein | | | $4.41 \times 10^4$ | | |
| M-CSF | | | $4.5 \times 10^4$ | | |
| $\alpha_1$-Antitrypsin | | | $4.5 \times 10^4$ | | |
| CD1 Membrane glycoprotein | | | $4.6 \times 10^4$ | | |
| Fab Fragment | | | $4.7 \times 10^4$ | | |
| High flux Dialyzer cut-off | | | | | |
| FactorVII Proconvertin | | | $5.0 \times 10^4$ | | |
| $\beta_2$-Glycoprotein I | | | $5.0 \times 10^4$ | | |
| $\alpha_1$B Glycoprotein | | | $5.0 \times 10^4$ | | |
| Factor I α | | | $5.0 \times 10^4$ | | |
| Transcortin | | | $5.07 \times 10^4$ | | |
| CD 2 membrane glycoprotein T lymph. | | | $5.0\text{-}5.8 \times 10^4$ | | |
| LMK kininogen | | | $5.0\text{-}6.8 \times 10^4$ | | |
| Ge-Globulin | | | $5.2 \times 10^4$ | | |
| Urokinase high M form | | | $5.4 \times 10^4$ | | |
| Thromboplastin FactorIII | | | $5.6 \times 10^4$ | | |
| Properdin | | | $5.6 \times 10^4$ | | |
| Factor X Stuart-Prower factor | | | $5.6 \times 10^4$ | | |
| Factor IX Plasma thromboplastin | | | $5.7 \times 10^4$ | | |
| Factor AtIII Heparin cofactor | | | $5.8 \times 10^4$ | | |
| Hemopexin | | | $5.7 \times 10^4$ | | |
| C1s Complement protein α | | | $5.8 \times 10^4$ | | |
| α-Antichymotrypsin | | | $5.8 \times 10^4$ | | |
| 3.8S-α-glycoprotein | | | $5.8 \times 10^4$ | | |
| Hemofilter cut-off | | | | | |
| $\alpha_2$HS-Glycoprotein | | | $5.9 \times 10^4$ | | |
| $\alpha_1$ T-Glycoprotein | | | $6.0 \times 10^4$ | | |
| Proalbumin | | | $6.1 \times 10^4$ | | |
| Prothrombin | | | $6.27 \times 10^4$ | | |
| $\alpha_2$-Antiplasmin | | | $6.3 \times 10^4$ | | |
| Thiroxine-binding globulin | | | $6.3 \times 10^4$ | | |
| $C_8$ α,β complement protein | | | $6.4 \times 10^4$ | | |
| CD 5 membrane glycoprotein | | | $6.5 \times 10^4$ | | |
| Klenow fragment | | | $6.8 \times 10^4$ | | |
| Hemoglobin | | | $6.8 \times 10^4$ | | |
| $\alpha_1$X-Glycoprotein | | | $6.8 \times 10^4$ | | |
| Protein S | | | $6.9 \times 10^4$ | | |
| Albumin | | | $6.9 \times 10^4$ | | |
| DAF decay accelerator | | | $7.0 \times 10^4$ | | |
| $\alpha_2$-Aniti plasmin | | | $7.0 \times 10^4$ | | |
| C9 Complement component | | | $7.1 \times 10^4$ | | |
| t_PA Tissue plasminogen activator | | | $7.2 \times 10^4$ | | |

TABLE 1-continued

BLOOD AND PLASMA COMPONENTS
SIZE BY MOLECULAR WEIGHT (DALTONS)

| COMPONENT | $\leq 10^3$ DAL. | $\leq 10^4$ DAL. | $\leq 10^5$ DAL. | $\leq 10^6$ DAL. | $\geq 10^6$ DAL. |
|---|---|---|---|---|---|
| Dextran | | | $7.5 \times 10^4$ | | |
| C5, C4, C3 Complement component β | | | $7.5 \times 10^4$ | | |
| Factor XII Hageman factor | | | $8.0 \times 10^4$ | | |
| Hemepoxin | | | $8.0 \times 10^4$ | | |
| $C_{1r}$ complement protein | | | $8.3 \times 10^4$ | | |
| Kallikrein | | | $8.8 \times 10^4$ | | |
| Interferon gamma receptor | | | $9.0 \times 10^4$ | | |
| Transferrin | | | $9.0 \times 10^4$ | | |
| Hmk kininogen | | | $8\text{-}11.4 \times 10^4$ | | |
| $\beta_2$-Glycoprotein II | | | $9.3 \times 10^4$ | | |
| C4 Complement component α | | | $9.3 \times 10^4$ | | |
| Sex binding Globulin | | | $9.4 \times 10^4$ | | |
| $Fab_2$ fragment | | | $9.5 \times 10^4$ | | |
| CR4 Complement receptor | | | $9.5\text{-}15 \times 10^4$ | | |
| Factor B | | | | $1 \times 10^5$ | |
| CALLA glycoprotein | | | | $1 \times 10^5$ | |
| Haptoglobin | | | | $1 \times 10^5$ | |
| DNA polymerase 1 | | | | $1.03 \times 10^5$ | |
| C1Inh glycoprotein | | | | $1 \times 10^5$ | |
| HMWK Kininogen | | | | $1.1 \times 10^5$ | |
| C7 Complement component | | | | $1.04 \times 10^5$ | |
| C1 inhibitor | | | | $1.05 \times 10^5$ | |
| C4 binding protein | | | | $1.07 \times 10^5$ | |
| C2 Complement | | | | $1.08 \times 10^5$ | |
| C-reactive protein | | | | $1.1 \times 10^5$ | |
| Integrins | | | | $1.1\text{-}1.3 \times 10^5$ | |
| E-LAM I adhesion molecule 1 | | | | $1.15 \times 10^5$ | |
| C5 Complement component α | | | | $1.15 \times 10^5$ | |
| C3 α | | | | $1.17 \times 10^5$ | |
| $C_6$ complement protein | | | | $1.24 \times 10^5$ | |
| Globulins (average) | | | | $1.4 \times 10^5$ | |
| CR2 Complement receptor | | | | $1.45 \times 10^5$ | |
| Factor H | | | | $1.5 \times 10^5$ | |
| IgG Immuneoglobulin | | | | $1.5 \times 10^5$ | |
| CR3 α Complement receptor | | | | $1.55 \times 10^5$ | |
| Factor XI (PTA) | | | | $1.6 \times 10^5$ | |
| Cefuloplasmin | | | | $1.6 \times 10^5$ | |
| IgA Immuneoglobulin | | | | $1.6 \times 10^5$ | |
| γG-Immuneoglobulin | | | | $1.6 \times 10^5$ | |
| IgD Immuneogloblin | | | | $1.75 \times 10^5$ | |
| Clathrin | | | | $1.8 \times 10^5$ | |
| Inter-α-trypsin inhibitor | | | | $1.8 \times 10^5$ | |
| IgE Immuneogloblin | | | | $1.9 \times 10^5$ | |
| Plasma filter cut-off | | | | | |
| Carcinoembryonic antigen | | | | $2.0 \times 10^5$ | |
| P complement (properdin) | | | | $2.2 \times 10^5$ | |
| CR1 Complement receptor | | | | $2.5 \times 10^5$ | |
| Fibronectin | | | | $2.5 \times 10^5$ | |
| Factor XIII Fibrin stabalizing factor | | | | $3.2 \times 10^5$ | |
| Factor V Proaccelerin | | | | $3.3 \times 10^5$ | |
| Cholinesterase | | | | $3.4 \times 10^5$ | |
| Fibrinogen | | | | $4.0 \times 10^5$ | |
| Cold insoluble globulin | | | | $4.5 \times 10^5$ | |
| α-$_1$ Lipoprotein  HDL$_3$ | | | | $1.9 \times 10^5$ | |
| HDL$_2$ | | | | $4.5 \times 10^5$ | |
| RNA polymerase | | | | $4.5\text{-}5 \times 10^5$ | |
| α$_2$-Macroglobulin | | | | $8.2 \times 10^5$ | |
| C1 complex | | | | | |
| IgM Immuneogloblulin | | | | $9 \times 10^5$ | |
| β-Lipoprotein (LDL) | | | | $9.55 \times 10^5$ | |
| α$_2$-Lippoprotein (LDL) | | | | | $3.2 \times 10^6$ |
| Factor VIII antihemophilic globulin | | | | | $5\text{-}20 \times 10^6$ |
| Lymphocyte | | | | | $8.3 \times 10^6$ |
| Megakaryocyte | | | | | $>10^6$ d = 8-12 μm |
| | | | | | $>10^6$ d = 35-160 μm |
| Lymphoid NK cells | | | | | d = 15 μm |
| Plasma cells | | | | | d = 14 μm |
| Platelet | | | | | d = 2-4 μm |
| Polymorphonuclear leukocyte | | | | | d = 13 μm |
| Erythrocytes | | | | | d = 7.5 μm |
| HIV virus Retroviridae | | | | | d = 80-130 nm |
| HBV virus Hepadnaviridae | | | | | d = 40 nm |
| CMV virus Herpesviridae | | | | | d = 150-200 nm |

TABLE 1-continued

BLOOD AND PLASMA COMPONENTS
SIZE BY MOLECULAR WEIGHT (DALTONS)

| COMPONENT | ≤$10^3$ DAL. | ≤$10^4$ DAL. | ≤$10^5$ DAL. | ≤$10^6$ DAL. | ≥$10^6$ DAL. |
|---|---|---|---|---|---|
| HCV virus Flaviridae | | | | | d = 40-50 nm |
| MuLV virus | | | | | d = 80-120 nm |
| Polio virus | | | | | d = 23-30 nm |
| Herpes Simplex virus | | | | | d = 120-150 nm |
| Aadenovirus | | | | | d = 70-90 nm |

What is claimed is:

1. Apparatus for carrying out patient fluid management comprising:
   an implantable filter device comprising a plurality of elongated hollow tubes and a plurality of elongated microporous fibers having an interior lumen extending along the length thereof, each fiber having a first and second end secured to different ones of said elongated hollow tubes, wherein the interior lumen of each of the fibers communicates with the interior of two of said hollow tubes, and wherein each of the elongated microporous fibers have an asymmetrical fiber wall morphology between the inner wall surface extending along the interior fiber lumen and the outer wall surface, said fiber wall having a higher mass density zone adjacent to the outer wall surface and a lower mass density zone adjacent to the inner wall surface, said higher mass density zone having a smaller average nominal pore size than the average nominal pore size in the lower mass density zone and wherein said fibers are configured to separate plasma from whole blood in-vivo by passing plasma through said fiber wall from the outer wall surface to the inner wall surface and to said interior lumen thereof;
   a multiple lumen catheter secured to the proximal end of the filter device having one or more lumens in fluid communication with the interior of said one or more hollow tubes and a plasma return lumen; and
   ultrafiltration apparatus having a sieving coefficient cutoff between about $1 \times 10^4$ and about $6 \times 10^4$ daltons and configured to separate plasma water and selected plasma components having molecular weights below the sieving coefficient cutoff point from the separated plasma, and tubing for directing plasma between said catheter and the ultrafiltration apparatus.

2. Apparatus of claim 1 wherein said multiple lumen catheter comprises a first lumen and a second lumen in fluid communication with the interior of said one or more hollow tubes and a third lumen comprising said plasma return lumen.

3. Apparatus of claim 1 including:
   a fluid control assembly comprising first tubing in fluid communication with said first lumen of said catheter and a first fluid pump cooperating therewith for directing plasma from said filter device, second tubing in fluid communication with said second lumen of said catheter and a second pump cooperating therewith for directing backflush fluid into said filter device, and third tubing in fluid communication with said third lumen of said catheter for directing plasma from the ultrafiltration apparatus to a patient; and
   control apparatus operatively communicating with said first and second pumps for controlling the operation thereof, respectively.

4. Apparatus of claim 3 including a third pump cooperating with said third tubing and in control connection with said control apparatus.

5. Apparatus of claim 3 including a source of backflush fluid cooperating with said second tubing.

6. Apparatus of claim 3 wherein said control apparatus comprises a microprocessor-controller including software programmed for operating said apparatus.

7. A filter device of claim 1 wherein each of said fibers are generally bowed along its length between said first and second ends to form an arch spaced apart from said one or more elongated hollow tubes and forming a passageway therebetween.

8. A filter device of claim 7 wherein said elongated microporous fibers comprise first and second fibers, said first fibers forming a first arch of spaced fibers extending over a first portion of said device, said second fibers forming a second arch extending over a second portion of said device, opposite the first portion, said first and second arches spaced apart from said one or more elongated hollow tubes to form passageways therebetween.

9. A filter device of claim 1 wherein the first and second ends of said elongated microporous fibers are secured to said one or more hollow tubes, respectively, at substantially regular intervals.

10. A filter device of claim 1 wherein the length of each of said elongated microporous fibers is between about 1 cm and about 4 cm.

11. A filter device of claim 1 wherein the first end of each elongated microporous fiber is offset longitudinally from the second end of each said fiber along the length of said one or more elongated hollow tubes whereby a straight line extending through the first and second end of a fiber forms an acute angle with one of said axes.

12. A filter device of claim 1 wherein the space between adjacent fibers is between about 0.1 cm and about 1.0 cm.

13. A filter device of claim 1 wherein the length of said one or more hollow tubes is between about 10 cm and about 25 cm.

14. Apparatus of claim 1 wherein the fiber wall structure comprises a continuous change in mass density from said outer wall surface to said inner wall surface and comprises a continuum of voids bounded by solid frames, said fiber wall having an asymmetrical pore size and asymmetrical mass density between said inner wall surface and the outer wall surface.

15. Apparatus of claim 3 including a container cooperating with said ultrafiltration apparatus for receiving effluent therefrom.

16. Apparatus of claim 15 including fourth tubing in fluid communication with said container and said ultrafiltration apparatus.

17. Apparatus of claim 16 including an effluent pump cooperating with said fourth tubing for pumping effluent from said ultrafiltration apparatus to said container.

18. Apparatus of claim 3 including a source of fresh plasma in fluid communication with said ultrafiltration apparatus and/or said third tubing.

19. Apparatus of claim 3 wherein said ultrafiltration apparatus has a sieving coefficient cutoff below the molecular weight of albumin.

20. Apparatus of claim 3 wherein said filter device has a sieving coefficient cutoff above the ultrafiltration sieving coefficient cutoff and below about $5 \times 10^6$ daltons.

21. Apparatus of claim 3 wherein said filter device has a sieving coefficient cutoff between about $6 \times 10^4$ daltons and about $2 \times 10^5$ daltons.

22. Apparatus of claim 21 wherein the fiber wall structure comprises a continuous change in mass density from said outer wall surface to said inner wall surface and comprises a continuum of voids bounded by solid frames, said fiber wall having an asymmetrical pore size and asymmetrical mass density between said inner wall surface and the outer wall surface.

23. Apparatus of claim 14 wherein said filter device has a sieving coefficient cutoff above the ultrafiltration sieving coefficient cutoff and below about $5 \times 10^6$ daltons.

24. Apparatus of claim 20 wherein said ultrafiltration apparatus has a sieving coefficient cutoff below the molecular weight of albumin.

25. Apparatus of claim 22 wherein said ultrafiltration apparatus has a sieving coefficient cutoff below the molecular weight of albumin.

26. A filter device of claim 1 comprising one or more first elongated hollow tubes and one or more second elongated hollow tubes extending substantially parallel along the length thereof, and wherein a first end of each of said elongated microporous fibers is secured to a first hollow tube and a second end of each of said fibers is secured to a second hollow tube whereby the interior fiber lumen of each fiber communicates with the interior of a first and a second hollow tube.

27. A method of patient fluid management and/or treating patient fluid overload comprising:
    separating plasma from whole blood in-vivo using a filter device comprising a plurality of elongated hollow tubes and a plurality of elongated microporous fibers having an interior lumen extending along the length thereof, each fiber having a first and second end secured to different ones of said elongated hollow tubes, wherein the interior lumen of each of the fibers communicates with the interior of two of the hollow tubes, and wherein the fiber wall morphology of each of the elongated microporous fibers is asymmetrical between the inner wall surface extending along the interior fiber lumen and the outer wall surface, said fiber wall having a higher mass density zone adjacent to the outer wall surface and a lower mass density zone adjacent to the inner wall surface, said higher mass density zone having a smaller average nominal pore size than the average nominal pore size in the lower mass density zone, and passing plasma through said fiber wall from the outer wall surface to the inner wall surface and to said interior lumen thereof;
    directing the separated plasma to an ultrafiltration apparatus having a sieving coefficient cutoff between about $1 \times 10^4$ and about $6 \times 10^4$ daltons and separating plasma water and selected plasma components having molecular weights at or below the sieving coefficient cutoff from said separated plasma; and
    returning the treated plasma to the patient.

28. A method of claim 27 comprising separating plasma water and plasma components having a molecular weight below the molecular weight of albumin from said separated plasma.

29. A method of claim 27 wherein said filter apparatus comprises a triple lumen catheter having said filter device on the proximal end thereof, and wherein separated plasma is directed from said filter device to said ultrafiltration apparatus through a first lumen of said triple lumen catheter and returned to the patient through a second lumen thereof.

30. A method of claim 29 including periodically backflushing said filter device via a third lumen of said triple lumen catheter.

31. A method of claim 27 including directing fresh plasma to the patient.

32. A method of patient fluid management and/or treating patient fluid overload comprising:
    securing a plasma filter apparatus comprising a filter device in a blood vessel of a patient, said filter device comprising a plurality of elongated hollow tubes and a plurality of elongated microporous fibers having an interior lumen extending along the length thereof, each fiber having a first and second end secured to different ones of said elongated hollow tubes, wherein the interior lumen of each of the fibers communicates with the interior of two of the hollow tubes, and wherein the fiber wall morphology of each of the elongated microporous fibers is asymmetrical between the inner wall surface extending along the interior fiber lumen and the outer wall surface, said fiber wall having a higher mass density zone adjacent to the outer wall surface and a lower mass density zone adjacent to the inner wall surface, said higher mass density zone having a smaller average nominal pore size than the average nominal pore size in the lower mass density zone;
    separating plasma from whole blood in-vivo by passing plasma through said fiber wall from the outer wall surface to the inner wall surface;
    directing the separated plasma to an ultrafiltration apparatus having a sieving coefficient cutoff between about $1 \times 10^4$ and about $6 \times 10^4$ daltons and separating plasma water and selected plasma components having molecular weights at or below the sieving coefficient cutoff from said separated plasma; and
    returning the treated plasma to the patient.

33. A method of claim 32 wherein said filter apparatus comprises a triple lumen catheter having said filter device on the proximal end thereof, and wherein separated plasma is directed from said filter device to said ultrafiltration apparatus through a first lumen of said triple lumen catheter and returned to the patient through a second lumen thereof.

34. A method of claim 33 including periodically backflushing said filter device via a third lumen of said triple lumen catheter.

35. Apparatus of claim 1 having a lower mass density zone characterized by a nominal average pore diameter of between about 1 μm and about 60 μm.

36. Apparatus of claim 1 having a higher mass density zone characterized by a nominal average pore diameter of between about 0.3 μm and about 1 μm.

37. Apparatus of claim 35 having a higher mass density zone characterized by a nominal average pore diameter of between about 0.3 μm and about 1 μm.

38. Apparatus of claim 37 wherein the nominal average pore diameter in said lower mass density zone is between about 2 μm and about 6 μm.

39. Apparatus of claim 38 wherein the nominal average pore diameter in said higher mass density zone is between about 0.4 μm and about 0.8 μm.

40. Apparatus of claim 37 having one or more intermediate mass density zones having a nominal average pore diameter of between about 0.8 μm and about 2 μm.

41. Apparatus of claim 38 having two intermediate mass density zones, a first intermediate zone having a nominal average pore diameter of between about 0.8 μm and about 1.2 μm and a second intermediate zone having a nominal average pore diameter of between about 1.2 μm and about 2 μm.

42. Apparatus of claim 1 wherein said fibers comprise a polysulfone fiber.

43. Apparatus of claim 14 wherein said fibers comprise a polysulfone fiber.

44. Apparatus of claim 22 wherein said fibers comprise a polysulfone fiber.

* * * * *

UNITED STATES PATENT AND TRADEMARK OFFICE
CERTIFICATE OF CORRECTION

PATENT NO. : 7,481,936 B2  
APPLICATION NO. : 11/078016  
DATED : January 27, 2009  
INVENTOR(S) : Gorsuch et al.

Page 1 of 2

It is certified that error appears in the above-identified patent and that said Letters Patent is hereby corrected as shown below:

Issued Patent     1. Description of Error

| Column | Line | |
|---|---|---|
| 1 | 25 | Change "heparinize" to --heparinized--. |
| 6 | 34 | Change "That" to --that--. |
| 7 | 10 | Change "CD" to --OD--. |
| 7 | 13 | Change "filly" to --fully--. |
| 7 | 21 | Change "polvethylene" to --polyethylene--. |
| 7 | 30 | Change "acetomide" to --acetamide--. |
| 7-8 | 13 (Approx.) (Table 1) | Change "Glysine" to --Glycine--. |
| 7-8 | 20 (Approx.) (Table 1) | Change "Billirubin" to --Bilirubin--. |
| 9-10 | 33 (Approx.) (Table 1) | Change "moleule" to --molecule--. |
| 9-10 | 34 (Approx.) (Table 1) | Change "glyoprotein" to --glycoprotein--. |
| 11-12 | 37 (Approx.) (Table 1) | Change "Immuneoglobulin" to --Immunoglobulin--. |
| 11-12 | 40 (Approx.) (Table 1) | Change "Cefuloplasmin" to --Ceruloplasmin--. |
| 11-12 | 41 (Approx.) (Table 1) | Change "Immuneoglobulin" to --Immunoglobulin--. |
| 11-12 | 42 (Approx.) (Table 1) | Change "Immuneoglobulin" to --Immunoglobulin--. |
| 11-12 | 43 (Approx.) (Table 1) | Change "Immuneogloblin" to --Immunoglobulin--. |

UNITED STATES PATENT AND TRADEMARK OFFICE
CERTIFICATE OF CORRECTION

PATENT NO. : 7,481,936 B2
APPLICATION NO. : 11/078016
DATED : January 27, 2009
INVENTOR(S) : Gorsuch et al.

It is certified that error appears in the above-identified patent and that said Letters Patent is hereby corrected as shown below:

| | | |
|---|---|---|
| 11-12 | 46 (Approx.) (Table 1) | Change "Immuneogloblin" to --Immunoglobulin--. |
| 11-12 | 62 (Approx.) (Table 1) | Change "Immuneogloblulin" to --Immunoglobulin--. |
| 11-12 | 64 (Approx.) (Table 1) | Change "Lippoprotein" to --Lipoprotein--. |
| 13-14 | 8 (Approx.) (Table 1) | Change "Aadenovirus" to --Adenovirus--. |

Signed and Sealed this

Second Day of June, 2009

JOHN DOLL
*Acting Director of the United States Patent and Trademark Office*